United States Patent
Lee et al.

(10) Patent No.: US 10,517,522 B2
(45) Date of Patent: Dec. 31, 2019

(54) SYSTEM FOR MEASURING LOWER EXTREMITY MUSCLE STRENGTH

(71) Applicants: KYUNGPOOK NATIONAL UNIVERSITY INDUSTRY-ACADEMIC COOPERATION FOUNDATION, Daehak-ro, Buk-gu, Daegu (KR); DAEGU GYEONGBUK INSTITUTE OF SCIENCE AND TECHNOLOGY, Techno jungang-daero, Hyeonpung-myeon, Dalseong-gun, Daegu (KR)

(72) Inventors: Yang Soo Lee, Daegu (KR); Sang Jun Moon, Daegu (KR)

(73) Assignee: Yang Soo Lee, Daegu (KR)

( * ) Notice: Subject to any disclaimer, the term of this patent is extended or adjusted under 35 U.S.C. 154(b) by 275 days.

(21) Appl. No.: 15/105,071

(22) PCT Filed: Dec. 17, 2014

(86) PCT No.: PCT/KR2014/012431
§ 371 (c)(1),
(2) Date: Jun. 16, 2016

(87) PCT Pub. No.: WO2015/093833
PCT Pub. Date: Jun. 25, 2015

(65) Prior Publication Data
US 2017/0000402 A1    Jan. 5, 2017

(30) Foreign Application Priority Data

Dec. 18, 2013 (KR) .................. 10-2013-0158016
May 28, 2014 (KR) .................. 10-2014-0064431

(51) Int. Cl.
A61B 5/22    (2006.01)
A61B 5/11    (2006.01)
A61B 5/00    (2006.01)

(52) U.S. Cl.
CPC ............ *A61B 5/224* (2013.01); *A61B 5/0077* (2013.01); *A61B 5/1127* (2013.01); *A61B 5/706* (2013.01);
(Continued)

(58) Field of Classification Search
CPC ... A61B 5/1116; A61B 5/1114; A61B 5/1121; A61B 5/1123; A61B 5/1124
See application file for complete search history.

(56) References Cited

U.S. PATENT DOCUMENTS 5,761,096 A * 6/1998 Zakutin ................. A63B 43/00
368/2
2004/0063083 A1* 4/2004 Rink ...................... G06Q 50/22
434/247
(Continued)

FOREIGN PATENT DOCUMENTS

JP    2008-092979    4/2008
KR    1020010095900    11/2001
(Continued)

OTHER PUBLICATIONS

International Search Report for PCT/KR2014/012431.

*Primary Examiner* — Patrick Fernandes
(74) *Attorney, Agent, or Firm* — STIP Law Group, LLC

(57) ABSTRACT

The present invention relates to a system for measuring lower extremity muscle strength, and more particularly, to a system for measuring lower extremity muscle strength which can effectively measure or train lower extremity muscle strength by means of a simpler method.

17 Claims, 8 Drawing Sheets

(52) U.S. Cl.
CPC .......... *A61B 5/742* (2013.01); *A61B 2505/09* (2013.01); *A61B 2562/0247* (2013.01); *A61B 2562/0261* (2013.01); *A61B 2576/00* (2013.01)

(56) References Cited

U.S. PATENT DOCUMENTS

| | | | |
|---|---|---|---|
| 2006/0085047 A1* | 4/2006 | Unsworth | A61N 1/36014 607/48 |
| 2010/0035728 A1* | 2/2010 | Shinomiya | A61B 5/1038 482/8 |
| 2011/0105956 A1* | 5/2011 | Hirth | A61B 5/1116 600/595 |
| 2012/0116258 A1* | 5/2012 | Lee | A61B 5/1071 600/595 |
| 2013/0012789 A1* | 1/2013 | Horseman | A61B 5/6887 600/301 |
| 2013/0179110 A1* | 7/2013 | Lee | A61B 5/1118 702/130 |

FOREIGN PATENT DOCUMENTS

| | | |
|---|---|---|
| KR | 1020100085114 | 7/2010 |
| KR | 1010568800000 | 8/2011 |
| KR | 1020120017948 | 2/2012 |

\* cited by examiner

[FIG. 1]
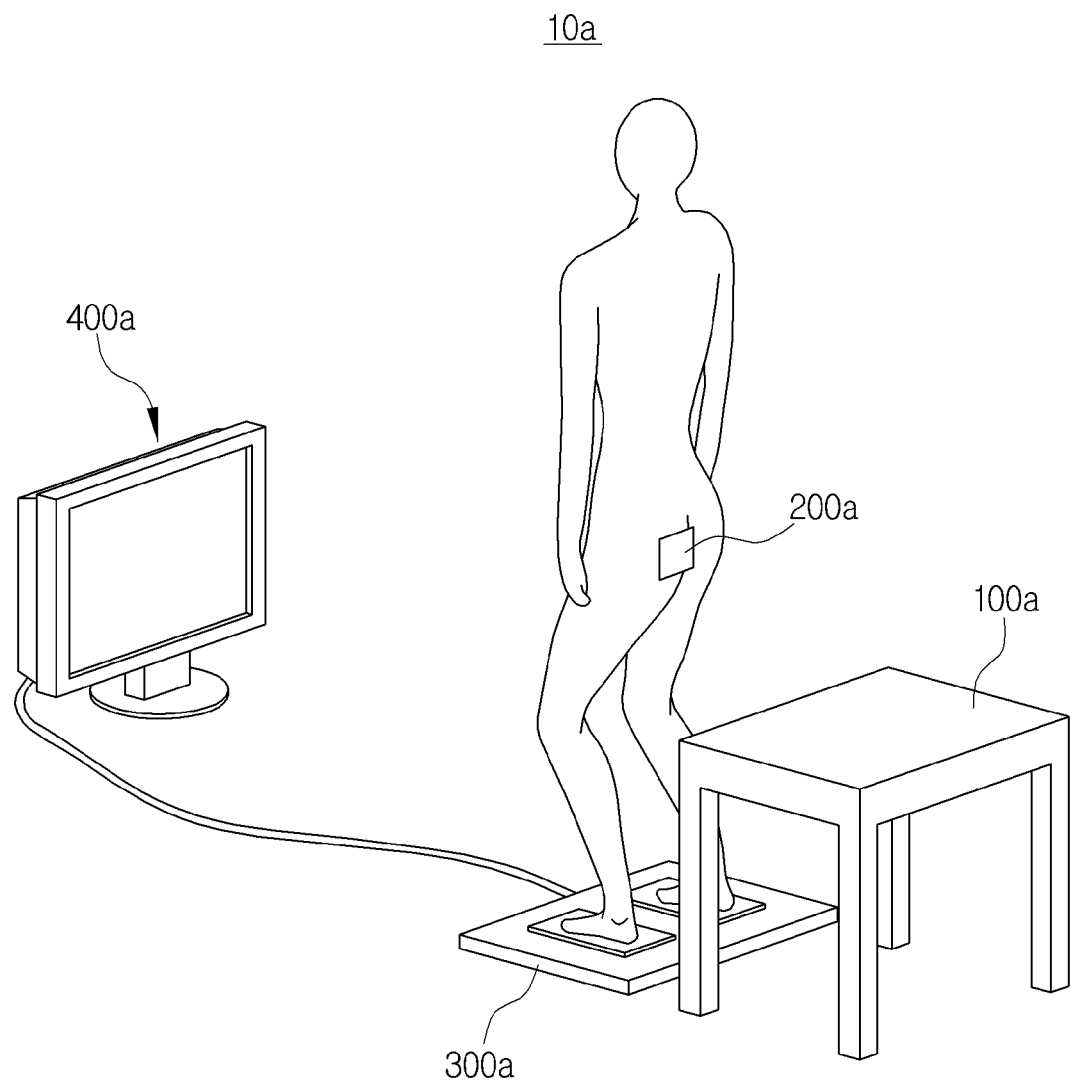

[FIG. 2]
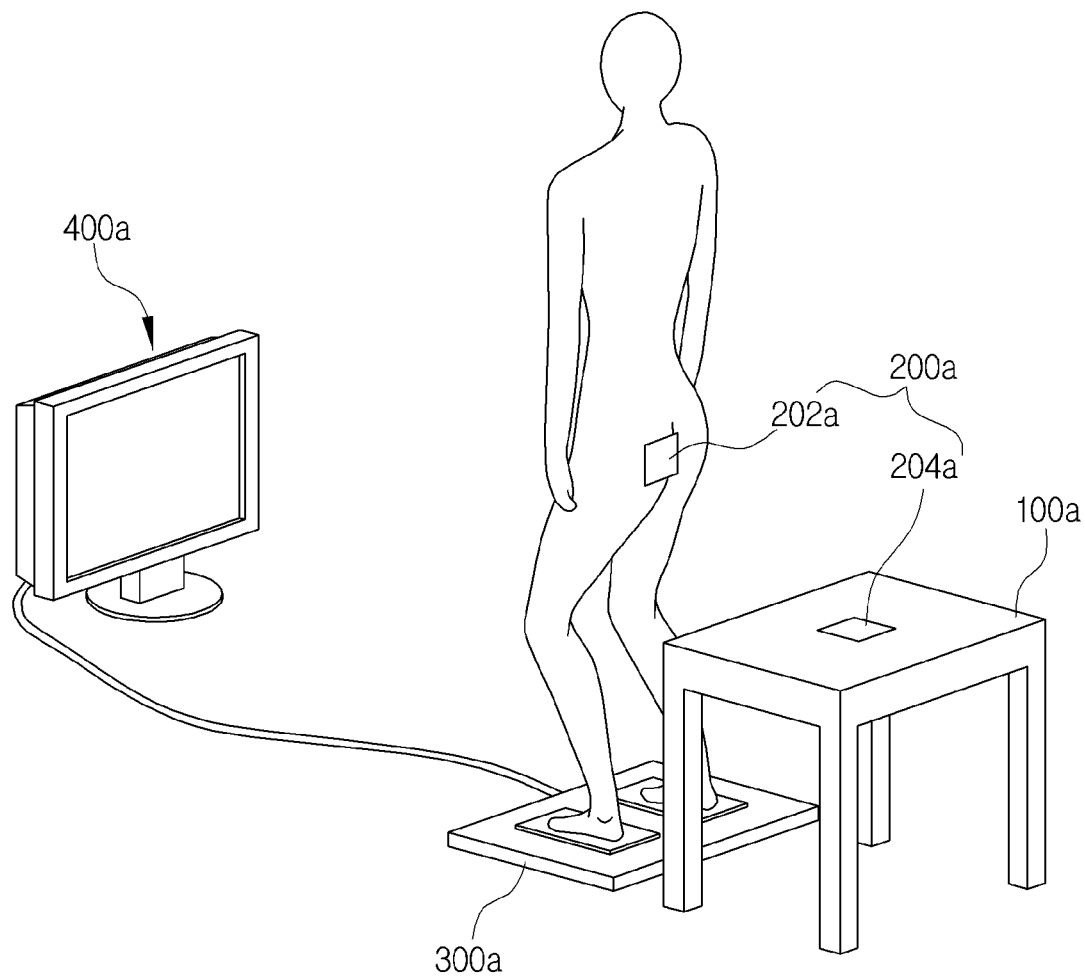

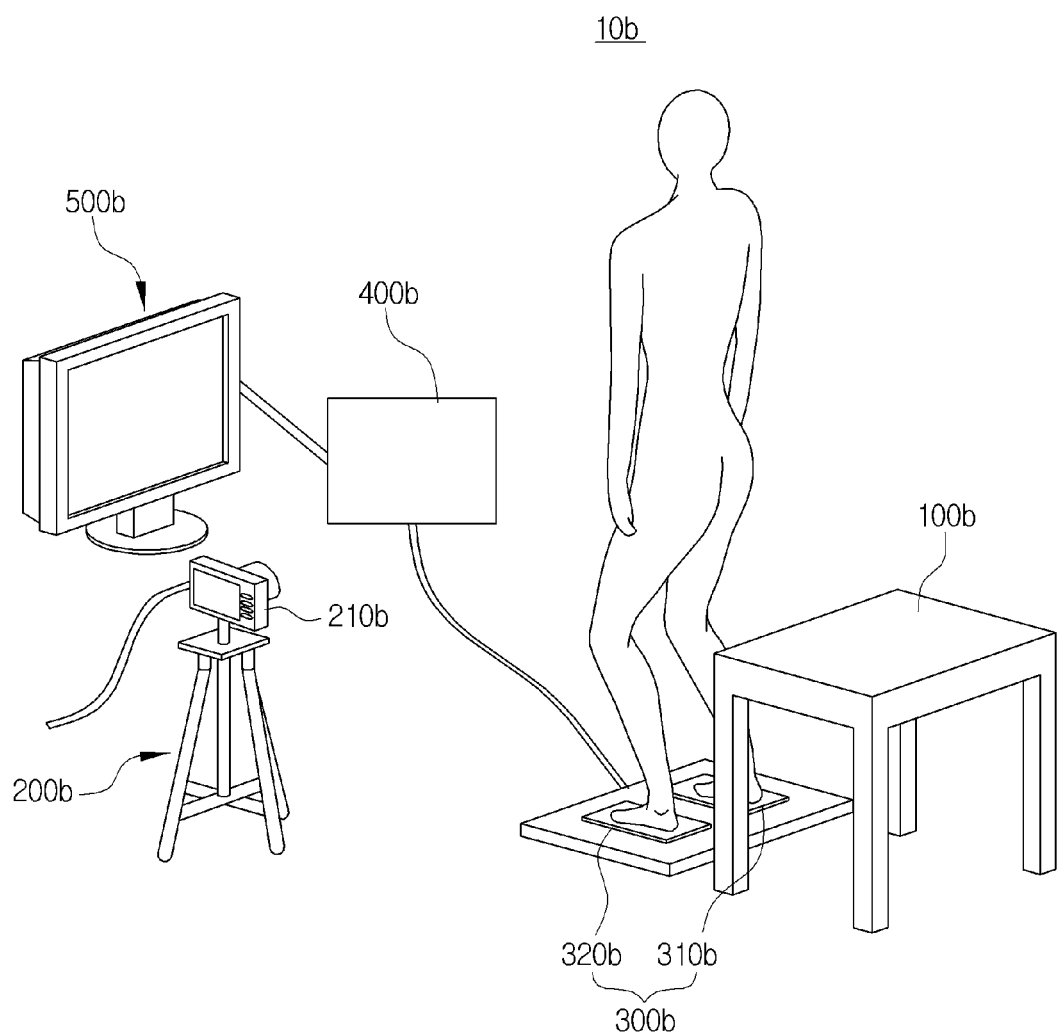
[FIG. 3]

[FIG. 4]
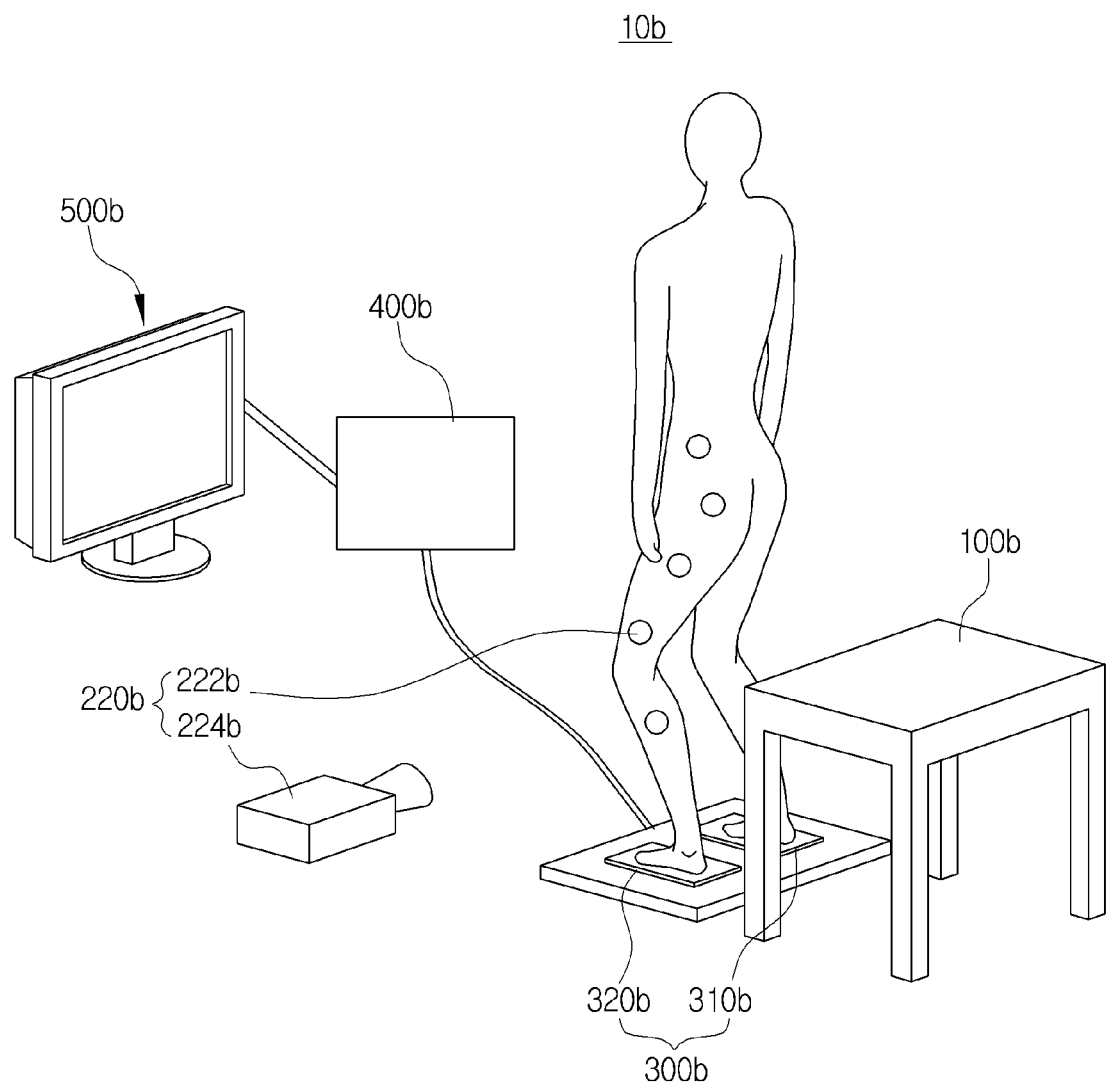

[FIG. 5]
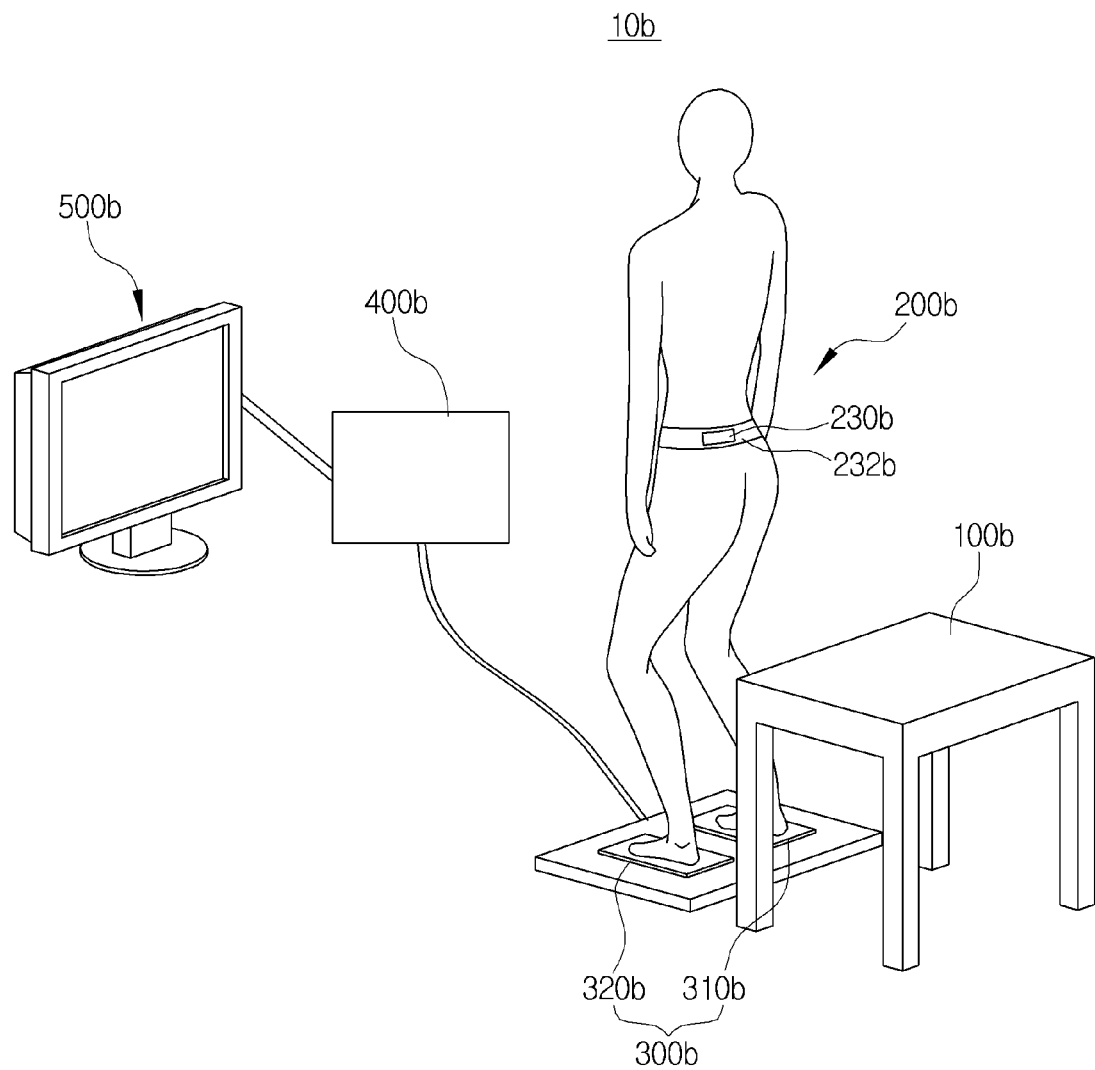

[FIG. 6]
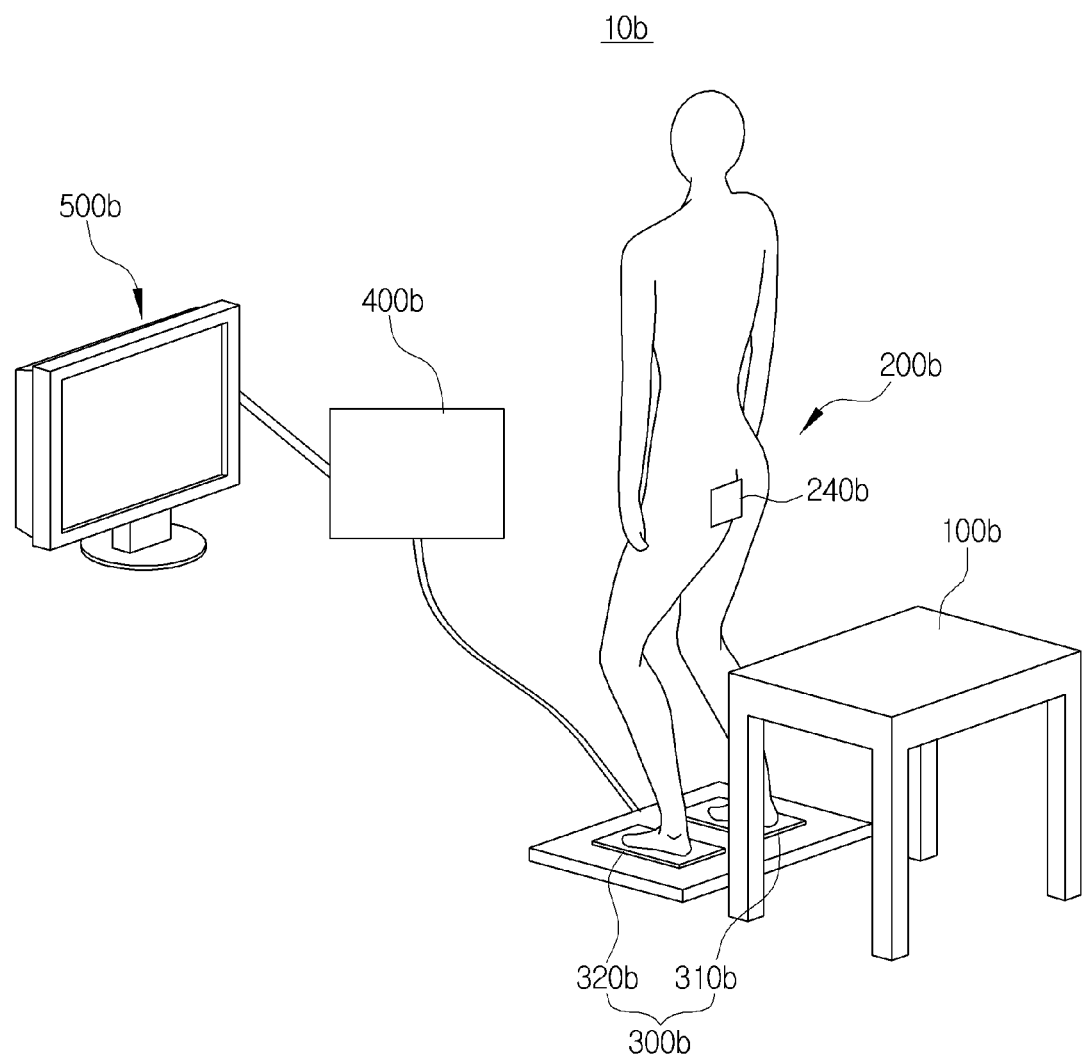

[FIG. 7]
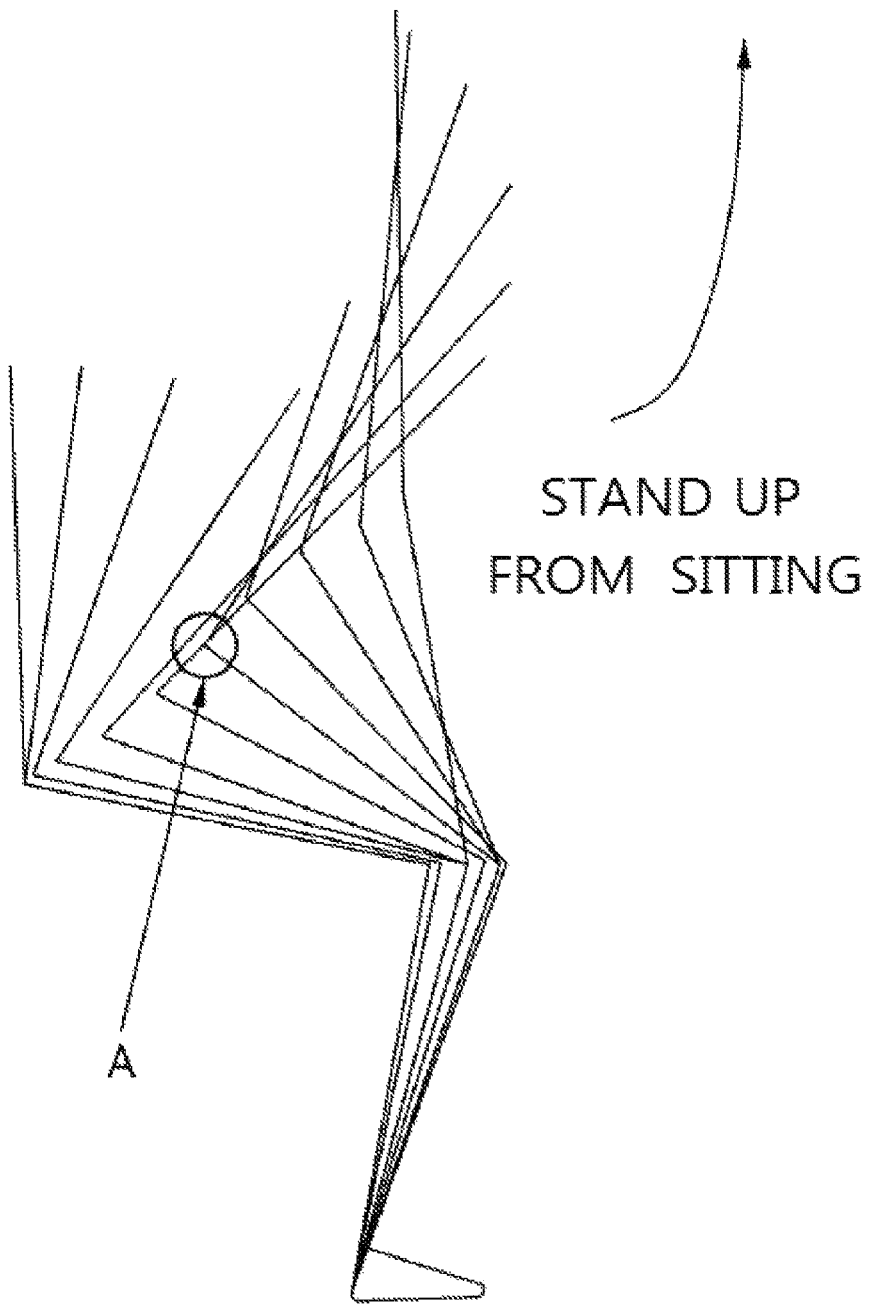

[FIG. 8]
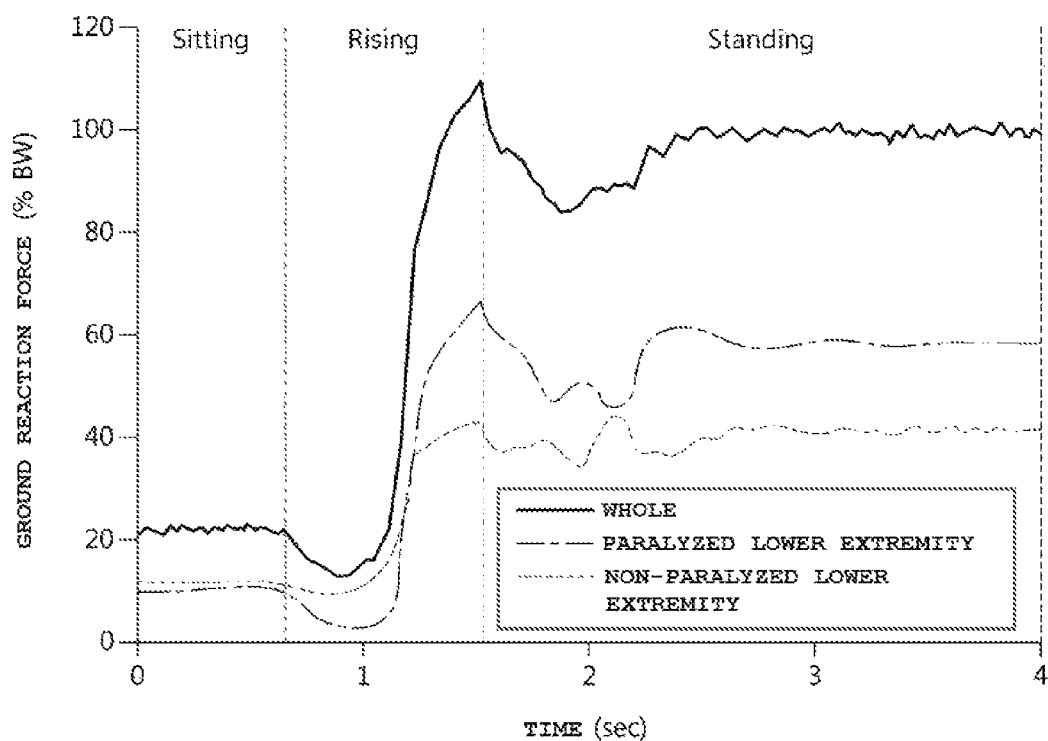

SYSTEM FOR MEASURING LOWER EXTREMITY MUSCLE STRENGTH

CROSS-REFERENCE TO RELATED APPLICATIONS

This application is the U.S. National Phase under 35 U.S.C. § 371 of International Application No. PCT/KR2014/012431 filed on Dec. 17, 2014, which in turn claims the benefit of Korean Application No. 10-2013-0158016, filed on Dec. 18, 2013, and Korean Application No. 10-2014-0064431, filed on May 28, 2014, the disclosures of which are incorporated by reference into the present application.

TECHNICAL FIELD

The present invention relates to a system for measuring lower extremity muscle strength, and more particularly, to a system for measuring lower extremity muscle strength which can effectively measure or train lower extremity muscle strength by means of a simpler method.

BACKGROUND ART

Measurement of muscle strength is an essential to check degree of muscle weakness and detects change of muscle strength.

To measure the muscle strength, a weight or a dynamometer has been often used.

There is a problem in that in the case of measuring the muscle strength using the weight, a plurality of instruments with various weights is required. And the dynamometer is expensive and requires a professional skill for use. Further, to measure extension muscle strength of the whole lower extremities, a dynamometer which is expensive and has a large space is required.

The larger the lower extremity muscle strength to be checked when a subject sits in a chair having a predetermined height and then rises, the subject may load more body weight to legs to be checked, but required muscle contraction is continuously changed to maintain load body weight to leg while the subject sits down and then stands up, and therefore the muscle strength cannot be measured by means of scales at both lower extremities.

In this case, a load extent of a body weight may be measured based on a ground reaction force.

When the subject sits in a chair and then rises, the largest muscle contraction of the lower extremities is occurring at the moment or near the moment that a body is separated from the chair. Therefore, the muscle strength may be measured based on the ground reaction force generated by the lower extremities to be measured at the moment that the body is separated from the chair.

Therefore, various researches into a rehabilitation device for evaluate muscle strength of muscle weakness paralysis symptoms and patients with paralysis symptoms have been conducted.

Korean Patent Laid-Open No. 10-2009-0117084 (filed on Nov. 30, 2009) discloses a user-customized gait rehabilitation device.

RELATED ART DOCUMENT

Patent Document

Korean Patent Laid-Open Publication No. 10-2009-0117084 (filed on Nov. 30, 2009)

DISCLOSURE

Technical Problem

An object of the present invention is to provide a system for measuring lower extremity muscle strength which can easily measure lower extremity muscle strength by means of a relatively simpler structure.

An object of the present invention is to provide a system for measuring lower extremity muscle strength which can measure lower extremity muscle strength and can be used for a lower extremity muscle strengthening exercise.

An object of the present invention is to provide a system for measuring lower extremity muscle strength which can more accurately measure lower extremity muscle strength by confirming timing when an object to be measured is separated from a sitting part.

An object of the present invention is to provide a system for measuring lower extremity muscle strength which can measure lower extremity muscle strength by allowing a subject to slowly rise while a body weight of the subject is maximally loaded to lower extremities to be measured and using the ground reaction force generated by the lower extremities whose muscle strength will be measured at timing when a hip or a thigh of an object to be measured is separated from a sitting part.

An object of the present invention is to provide a system for measuring lower extremity muscle strength which may be used to strengthen muscle strength by loading a predetermined body weight to load extremities whose muscle strength needs to be strengthened to allow a subject to rise.

An object of the present invention is to provide a system for measuring lower extremity muscle strength which can measure maximum lower extremity extension muscle strength by means of a table prepared using an exercise analysis and a moving speed, a height, a body weight, a height of a sitting part, and a ratio of left and right ground reaction forces.

An object of the present invention is to provide a system for measuring lower extremity muscle strength which can effectively figure out timing when an object to be measured is separated from a sitting part by means of a camera, a motion capturer, a motion sensor, a switch, or the like.

An object of the present invention is to provide a system for measuring lower extremity muscle strength which can predict timing when an object to be measured is separated from a sitting part from the moment that a trunk of an object to be measured is bent and then extended.

An object of the present invention is to provide a system for measuring lower extremity muscle strength which can measure a paralysis degree of lower extremity muscle strength and lower extremity muscle strength based on a size and a ratio of left and right ground reaction forces of lower extremities at timing when an object to be measured is separated from a sitting part.

An object of the present invention is to provide a system for measuring lower extremity muscle strength which can measure a paralysis degree of lower extremity muscle strength and lower extremity muscle strength based on an area drawn by a ground reaction force.

An object of the present invention is to provide a system for measuring lower extremity muscle strength which can train lower extremities based on a size and a ratio of left and right ground reaction forces.

Technical Solution

In one general aspect, a system for measuring lower extremity muscle strength, includes: a sitting part on which an object to be measured sits; a sensing unit mounted on the sitting part or at a portion of the object to be measured contacting the sitting part; and a ground reaction force measuring unit measuring a ground reaction force generated by the lower extremity of the object to be measured, in which the sensing unit may sense whether the object to be measured is separated from the sitting part.

The sensing unit may sense the moment that a hip or a thigh of the object to be measured is attached on the sitting part and is separated from the sitting part.

The sensing unit may be provided as a switch which is mounted at a hip or a thigh of the object to be measured and is detachable and when the hip or the thigh of the object to be measured is separated from the sitting part, the switch may be switched to an on or off state.

The sensing unit may be provided as a switch which is mounted at a hip or a thigh of the object to be measured and is detachable and provide information on timing when the hip or the thigh of the object to be measured is separated from the sitting part.

The sensing unit may include: a first sensing element mounted at a hip or a thigh of the object to be measured; and a second sensing element mounted at a position contacting the first sensing element at the sitting part.

The ground reaction force measuring unit may include: a first ground reaction force measuring unit provided at one lower extremity; and a second ground reaction force measuring unit provided at the other lower extremity, in which the first ground reaction force measuring unit and the second ground reaction force measuring unit may measure ground reaction forces generated by the lower extremities, respectively.

The ground reaction force measuring unit may include a piezoelectric plate or a strain gauge.

The system may further include: a control unit, in which the control unit may confirm a ground reaction force when the object to be measured is separated from the sitting part.

The system may further include: a control unit, in which the control unit may calculate the lower extremity muscle strength based on a ground reaction force measured by the ground reaction force measuring unit.

In another general aspect, a system for measuring lower extremity muscle strength, includes: a sitting part on which an object to be measured sits; a posture measuring unit measuring a posture of the object to be measured; and a ground reaction force measuring unit disposed at a lower portion of the object to be measured and measuring a ground reaction force generated by a lower extremity of the object to be measured, in which the lower extremity muscle strength of the object to be measured may be measured based on a ground reaction force at the moment that the object to be measured is separated from the sitting part.

The posture measuring unit may be provided as a camera and sense the moment that the object to be measured is separated from the sitting part by means of the camera.

The posture measuring unit may be provided as a motion capturer and sense the moment that the object to be measured is separated from the sitting part by means of the motion capturer.

The posture measuring unit may be provided as a motion sensor including a gyro sensor or an acceleration sensor and sense the moment that the object to be measured is separated from the sitting part by means of the motion sensor.

The posture measuring unit may be provided as a switch mounted at a hip of the object to be measured and when the hip of the object to be measured is separated from the sitting part, the switch may be switched to an on or off state.

The ground reaction force measuring unit may include: a first measurement element provided at a lower portion of one lower extremity; and a second measurement element provided at a lower portion of the other lower extremity, in which the first measurement element and the second measurement element may measure the ground reaction forces of the lower extremities, respectively.

The system for measuring lower extremity muscle strength may evaluate muscle strength of lower extremities based on a ratio of a first ground reaction force measured by the first measurement element and a second ground reaction force measured by the second measurement element.

The system may further include: a control unit, in which the control unit may calculate the lower extremity muscle strength based on a ground reaction force measured by the ground reaction force measuring unit.

The control unit may be connected to a display unit and contents analyzed or determined by the control unit may be fed back in real time through the display unit.

The system for measuring lower extremity muscle strength may access a game server to interact with a game or Internet based virtual world to train the lower extremities. The ground reaction force measuring unit may include a pressure sensor, a piezoelectric plate or a strain gauge.

Advantageous Effects

The system for measuring lower extremity muscle strength according to the present invention having the configuration as described above may include the relatively simpler structure to easily measuring the lower extremity muscle strength.

The system for measuring lower extremity muscle strength according to the embodiment of the present invention may be used for the muscle strengthening exercise of the lower extremity as well as may measure the lower extremity muscle strength.

The system for measuring lower extremity muscle strength according to the embodiment of the present invention may more accurately measure the lower extremity muscle strength by confirming the timing when the body of the object to be measured is separated from the sitting part.

The system for measuring lower extremity muscle strength according to the embodiment of the present invention may measure the lower extremity muscle strength by allowing the subject to slowly rise while the body weight of the subject is maximally loaded to the lower extremities to be measured and using the ratio or proportion of left and right ground reaction forces generated by the lower extremities whose muscle strength will be measured at the timing when a hip or a thigh of an object to be measured is separated from a sitting part.

The system for measuring lower extremity muscle strength according to the embodiment of the present invention may be used to strengthen the muscle strength by loading the predetermined body weight to the lower extremities whose the muscle strength needs to be strengthened to allow the subject to rise.

The system for measuring lower extremity muscle strength according to the embodiment of the present invention may measure the maximum lower extremity extension muscle strength by means of the table prepared using the exercise analysis, the moving speed, the height, the body weight, the height of the sitting part, and the ratio of left and right ground reaction forces.

The system for measuring lower extremity muscle strength according to the embodiment of the present invention may effectively figure out the timing when the object to be measured is separated from the sitting part by means of the camera, the motion capturer, the motion sensor, the switch, or the like.

The system for measuring lower extremity muscle strength according to the embodiment of the present invention may predict the timing when the object to be measured is separated from the sitting part from the moment that the trunk of the object to be measured is bent and then extended.

The system for measuring lower extremity muscle strength according to the embodiment of the present invention may measure the paralysis degree of the lower extremity muscle strength and the lower extremity muscle strength based on the ratio of left and right ground reaction forces of the lower extremities at the timing when the object to be measured is separated from the sitting part.

The system for measuring lower extremity muscle strength according to the embodiment of the present invention may measure the paralysis degree of the lower extremity muscle strength and the lower extremity muscle strength based on the area drawn by the ground reaction force.

The system for measuring lower extremity muscle strength according to the embodiment of the present invention may train the lower extremities based on the size and the ratio of left and right ground reaction forces.

It is possible to easily train the lower extremities by providing the method for performing game based on the ratio and the size of the body weight load of the respective lower extremities.

For example, it is possible to train the lower extremities by performing game while moving the cursor left and right based on the left and right ratio and moving the cursor up and down based on the size of the ground reaction force applied to the scale.

DESCRIPTION OF DRAWINGS

FIG. 1 is a diagram illustrating a system for measuring lower extremity muscle strength according to an embodiment of the present invention.

FIG. 2 is a diagram illustrating an appearance in which another type of sensing unit is mounted in the system for measuring lower extremity muscle strength according to the embodiment of the present invention.

FIG. 3 is a diagram illustrating a system for measuring lower extremity muscle strength according to another embodiment of the present invention.

FIG. 4 is a diagram illustrating an appearance in which the sensing unit is provided as a motion capturer in the system for measuring lower extremity muscle strength according to another embodiment of the present invention.

FIG. 5 is a diagram illustrating an appearance in which the sensing unit is provided as a motion sensor in the system for measuring lower extremity muscle strength according to another embodiment of the present invention.

FIG. 6 is a diagram illustrating an appearance in which the sensing unit is provided as a switch in the system for measuring lower extremity muscle strength according to another embodiment of the present invention.

FIG. 7 is a diagram illustrating an appearance in which a trunk of an object to be measured is bent and then extended.

FIG. 8 is a graph illustrating a change in a ground reaction force over time.

BEST MODE

Hereinafter, a system for measuring lower extremity muscle strength according to the present invention will be described in detail with reference to the accompanying drawings. The accompanying drawings to be provided below are provided by way of example so that the idea of the present invention can be sufficiently transferred to those skilled in the art to which the present invention pertains. Therefore, the present invention is not limited to the accompanying drawings to be provided below, but may be implemented in other forms. In addition, like reference numerals denote like elements throughout the specification.

Technical terms and scientific terms used in the present specification have the general meaning understood by those skilled in the art to which the present invention pertains unless otherwise defined, and a description for the known function and configuration unnecessarily obscuring the gist of the present invention will be omitted in the following description and the accompanying drawings.

In addition, the system means a set of components including apparatuses, mechanisms, units, etc. which are organized and regularly interact with each other to perform required functions.

First Embodiment

FIG. 1 is a diagram illustrating a system for measuring lower extremity muscle strength according to an embodiment of the present invention and FIG. 2 is a diagram illustrating an appearance in which another type of sensing unit is mounted in the system for measuring lower extremity muscle strength according to the embodiment of the present invention.

Referring to FIG. 1, a system 10a for measuring lower extremity muscle strength according to an embodiment of the present invention may include a sitting part 100a, a sensing unit 200a, and a ground reaction force measuring unit 300a.

The sitting part 100a may be provided so that an object to be measured can sit. For example, the sitting part 100a may be provided as a chair.

FIG. 1 illustrates the sitting part 100a in a chair form, but the sitting part 100a is not limited thereto. For example, as long as the object to be measured can sit, any sitting part is possible.

Further, the sitting part 100a or a portion of the object to be measured contacting the sitting part may be provided with the sensing unit 200a.

The sensing unit 200a is to sense whether the object to be measured contacting the sitting part 100a is separated from the sitting part 100a.

In this case, the sensing unit 200a may be mounted on the sitting part 100a or at a hip of the object to be measured.

However, the mounting position of the sensing unit 200a is not limited thereto, and therefore as long as the sensing unit 200a is at a position which may sense that the object to be measured is separated from the sitting part 100a when the object to be measured rises, the sensing unit 200a may be mounted anywhere.

For example, the sensing unit 200a may be mounted at a thigh of the object to be measured to sense timing when a body part is detached or separated from the sitting part 100a of the object to be measured according to whether the thigh contacts the sitting part 100a.

Further, the sensing unit 200a may be simultaneously mounted at a hip and a thigh.

Further, the sensing unit 200a is provided in a detachable switch form to be mounted at a desired position of the object to be measured and may be switched to an on or off state when the body part of the object to be measured is detached or separated from the sitting part 100*a*. By doing so, the timing when the body part of the object to be measured is detached or separated from the sitting part 100*a* may be sensed.

In detail, the sensing unit 200*a* is mounted at a hip or a thigh of the object to be measured, and thus the sensing unit 200*a* is switched from an on state to an off state when the object to be measured stands up from the sitting part 100*a* in the state in which it sits. As a result, the sensing unit 200*a* may sense the moment that the object to be measured stands up from the sitting part 100*a*.

Further, the sensing unit 200*a* may be provided as a force sensor including a piezoelectric sensor, and thus may sense the moment that the object to be measured is separated from the sitting part 100*a* based on a change in strength of a force applied to a sensor by the object to be measured when the object to be measured stands up.

In detail, when the object to be measured stands up from the sitting part 100*a* in the state which it sits, the force sensor of the sensing unit 200*a* may not sense a force and may confirm the moment that the change in force happens. As a result, it may determine the moment that the object to be measured is separated from the sitting part 100*a*.

Further, as illustrated in FIG. 2, the sensing unit 200*a* may be configured to include a first sensing element 202*a* and a second sensing element 204*a*.

The first sensing element 202*a* may be mounted at the hip or thigh of the object to be measured and the second sensing element 204*a* may be mounted at a position contacting the first sensing element 202*a* at the sitting part 100*a*.

When the object to be measured stands up from the sitting part 100*a*, the first sensing element 202*a* and the second sensing element 204*a* may generate a change in an electrical signal corresponding thereto by a non-contact or a non-pressure, such that it may determine the moment that the first sensing element 202*a* and the second sensing element 204*a* do not contact with each other, in detail, the moment that the object to be measured is separated from the sitting part 100*a*.

Further, the ground reaction force measuring unit 300*a* may be provided at lower extremities of the object to be measured.

The ground reaction force measuring unit 300*a* is to measure the ground reaction force generated by the lower extremities of the object to be measured. For example, the ground reaction force measuring unit 300*a* may be provided as a piezoelectric plate or a strain gauge and may be disposed under a sole of the object to be measured.

However, a form and a disposition of the ground reaction force measuring unit 300*a* are not limited thereto, and therefore the ground reaction force measuring unit 300*a* may have various forms and may be disposed at various positions.

The ground reaction force measuring unit 300*a* may include a first ground reaction force measuring unit 310*a* provided under a right lower extremity of the object to be measured, for example, a right sole and a second ground reaction force measuring unit 320*a* provided under a left lower extremity of the object to be measured, for example, a left sole.

The first ground reaction force measuring unit 310*a* may measure the ground reaction force of the object to be measured generated by the right lower extremity and the second ground reaction force measuring unit 320*a* may measure the ground reaction force of the object to be measured generated by the left lower extremity.

For example, when the object to be measured sitting on the sitting part 100*a* is instructed to stand up as slowly as possible while applying a body weight load to the right lower extremity as much as possible, if the muscle strength of the right lower extremity of the object to be measured is good, the object to be measured may stand up while applying most of the body weight load to the right lower extremity. However, if the muscle strength of the right lower extremity of the object to be measured is not good, the object to be measured may stand up while applying only some of the body weight load to the right lower extremity. This is represented by a difference in the ratio of ground reaction forces.

As such, it is possible to measure the lower extremity muscle strength as well as a paralysis state and an exercise state of the lower extremities based on a ratio of left and right ground reaction forces measured by the ground reaction force measuring unit 300*a*.

Further, the system for measuring lower extremity muscle strength according to the embodiment of the present invention may include a control unit 400*a*.

The control unit 400*a* may be prepared as, for example, a computer (may be prepared as portable terminals such as a smart phone in addition to a computer) and may process the measured data and display the processed results.

In detail, the control unit 400*a* may confirm the ratio of left and right ground reaction forces when the object to be measured is detached or separated from the sitting part 100*a*, for example, when the object to be measured stands up.

The foregoing sensing unit 200*a* or the first and second sensing elements 212*a* and 214*a* senses the moment that the object to be measured is separated from the sitting part 100*a* and transmits the sensed moment to the control unit 400*a* and transfers the ground reaction force measured by the ground reaction force measuring unit 300*a* to the control unit 400*a*, thereby confirming the ground reaction force when the object to be measured is separated.

Further, the control unit 400*a* may calculate the lower extremity muscle strength based on the ratio of left and right ground reaction forces measured by the ground reaction force measuring unit 300*a*, a moving speed, a body weight, a height of a sitting part (chair), a height, or the like.

In this case, an operation equation which may induce the ratio of left and right ground reaction forces as the lower extremity muscle strength may be previously set in the control unit 400*a* and the body weight, the height of the sitting part (chair), and the height of the object to be measured may also be input in advance.

In the case of measuring the muscle strength of the right lower extremity, the object to be measured rises as slow as possible while supporting its own body weight to the right lower extremity as much as possible, and as a result, the muscle strength of the right lower extremity may be measured based on the ratio of ground reaction force generated.

To the contrary, in the case of measuring the muscle strength of the left lower extremity, the object to be measured rises as slow as possible while supporting its own body weight to the left lower extremity as much as possible, and as a result, the muscle strength of the left lower extremity may be measured based on the ratio of ground reaction force generated.

Further, the object to be measured may access a game server to interact with a game or Internet based virtual world, and therefore is having fun while doing the lower extremity muscle strength exercise, thereby effectively increasing the lower extremity muscle strength.

As such, the system for measuring lower extremity muscle strength according to the embodiment may easily measure the lower extremity muscle strength by means of a relatively simpler structure, may be used for the muscle strengthening exercise of the lower extremities, and may more accurately measure the lower extremity muscle strength by confirming the timing when the object to be measured is separated from the sitting part.

Second Embodiment

FIG. 3 is a diagram illustrating a system for measuring lower extremity muscle strength according to another embodiment of the present invention, FIG. 4 is a diagram illustrating an appearance in which the sensing unit is provided as a motion capturer in the system for measuring lower extremity muscle strength according to another embodiment of the present invention, FIG. 5 is a diagram illustrating an appearance in which the sensing unit is provided as a motion sensor in the system for measuring lower extremity muscle strength according to another embodiment of the present invention, FIG. 6 is a diagram illustrating an appearance in which the sensing unit is provided as a switch in the system for measuring lower extremity muscle strength according to another embodiment of the present invention, FIG. 7 is a diagram illustrating an appearance in which a trunk of an object to be measured is bent and then extended, and FIG. 8 is a graph illustrating a ground reaction force over time.

Referring to FIG. 3, a system 10b for measuring lower extremity muscle strength according to another embodiment of the present invention may include a sitting part 100b, a posture measuring unit 200b, a ground reaction force measuring unit 300b, a control unit 400b, and a display unit 500b.

The sitting part 100b may be provided so that the object to be measured can sit. For example, the sitting part 100b may be provided as a chair.

FIG. 3 illustrates the sitting part 100b in a chair form, but the sitting part 100b is not limited thereto. For example, as long as the object to be measured can sit, any sitting part is possible.

A position adjacent to some of a body of the object to be measured or the object to be measured may be provided with the posture measuring unit 200b.

The posture measuring unit 200b may measure the posture of the object to be measured, in particular, is to sense whether the object to be measured is separated from the sitting part 100b.

In particular, referring to FIG. 3, the posture measuring unit 200b may be provided as a camera 210b. The camera 210b may serve to photograph the object to be measured.

In detail, the object to be measured is attached with a plurality of markers (not illustrated), and thus may transmit positional information on a place to which the markers are attached to the camera 210b.

In this case, the plurality of markers may use infrared rays to transmit the positional information on the place to which the markers are attached. The markers may be implemented as infrared markers which may directly diverge or reflect infrared rays to transmit an infrared signal to the camera 210b so as to transmit the positional information on the place to which the markers are attached.

As such, the appearance that the object to be measured rises from the sitting part 100b may be measured by means of the camera 210b, and as a result, it is possible to effectively determine the timing when the object to be measured is separated from the sitting part 100b.

Further, referring to FIG. 4, the posture measuring unit 200b may be provided as a motion capturer 220b.

The motion capturer 220b may include a patch 222b mounted in the object to be measured and a camera 224b which may recognize a position of the patch 222b to capture a motion of the object to be measured. In this case, the patch 222b may be attached to joints at the lower extremities and upper and lower portions of the joints.

Further, the motion information of the object to be measured which is measured by the motion capturer 220b may be reproduced in images such as animation, movie, game, or the like.

In detail, as illustrated in FIG. 7, to allow the object to be measured to rise from the sitting part 100b, an upper body of the object to be measured needs to be bent forward and then unfolded, and therefore the motion capturer 220b figures out the moment that the body of the object to be measured is bent forward and then unfolded, thereby effectively determining the timing when the object to be measured is separated from the sitting part 100b.

Further, referring to FIG. 5, the posture measuring unit 200b may be provided as a motion sensor 230b.

The motion sensor 230b may include a gyro sensor which may sense a speed and a position of the object to be measured, an acceleration sensor which may sense a change in the speed of the object to be measured, or the like.

For example, the motion sensor 230b may be mounted at a waist of the object to be measured.

In this case, the motion sensor 230b may be provided within a band 232b to be mounted at the waist of the object to be measured.

When the motion sensor 230b is mounted at the waist of the object to be measured, the motion sensor 230b may use the motion of the object to be measured to sense timing when the muscle contraction of the lower extremities happens as much as possible.

However, the mounting position of the motion sensor 230b is not limited thereto, and therefore as long as the motion sensor 230b is at a position which may effectively sense the timing when the trunk is bent and then extended when the object to be measured rises, the motion sensor 230b may be positioned anywhere.

In this case, the timing when the trunk of the object to be measured is bent and then extended may coincide with the timing when the object to be measured is separated from the sitting part 100b.

In detail, referring to FIG. 7, to allow the object to be measured to rise from the sitting part 100b, the upper body of the object to be measured is bent forward and then unfolded, and at the same time the lower extremities of the object to be measured may be unfolded in the state in which they are bent.

In this case, point A may be a waist portion of the object to be measured at which the motion sensor 230b is mounted.

As such, the timing when the trunk of the object to be measured is bent and then extended may be the timing when the object to be measured is separated from the sitting part 100b. By doing so, it is possible to effectively determine the timing when the object to be measured is separated from the sitting part 100b.

Further, referring to FIG. 6, the posture measuring unit 200b may be provided as a switch 240b which may be mounted at the hip of the object to be measured.

FIG. 6 illustrates that the switch 240b is mounted at the hip of the object to be measured but the switch may be of course mounted on the sitting part 100b.

Therefore, the mounting position of the switch 240b is not limited thereto, and therefore as long as the switch 240b is at a position which may sense that the object to be measured is separated from the sitting part 100*b* when the object to be measured rises, the switch 240*b* may be mounted anywhere.

For example, the switch 240*b* may be mounted at the hip or the thigh of the object to be measured to sense the timing when the object to be measured is separated from the sitting part 100*b* according to whether the sitting part 100*b* contacts the hip or the thigh.

Further, the switch 240*b* is detachably provided so that the switch 240*b* may be mounted at the desired position of the object to be measured and may be switched from an on state to an off state when the object to be measured is separated from the sitting part 100*b*. By doing so, it is possible to effectively figure out the timing when the object to be measured is separated from the sitting part 100*b*.

As such, the system 10*b* for measuring lower extremity muscle strength according to another embodiment of the present invention may include the posture measuring unit 200*b* in various forms to effectively figure out the timing when the object to be measured is separated from the sitting part 100*b*.

In this case, the timing when the object to be measured is separated from the sitting part 100*b* has something to do with the size of the ground reaction force.

For example, the size of the ground reaction force is small and may be little changed in the state in which the object to be measured sits on the sitting part 100*b*. On the other hand, the size of the ground reaction force may be suddenly increased at the timing when the object to be measured is separated from the sitting part 100*b*.

Therefore, it is possible to predict the timing when the object to be measured is separated from the sitting part 100*b* based on the size of the ground reaction force.

Further, the case in which the posture measuring unit 200*b* is provided as the camera 210*b*, the motion capturer 220*b*, the motion sensor 230*b*, or the switch 240*b* is described as an example with reference to FIGS. 3 to 6, but the posture measuring unit 200*b* is not limited thereto. Therefore, any posture measuring unit which may measure the posture of the object to be measured may be used.

In addition, FIGS. 3 to 6 illustrate that the camera 210*b*, the motion capturer 220*b*, the motion sensor 230*b*, or the switch 240*b* is separately provided but all of them may be of course used together.

To measure the ground reaction force, the object to be measured may be provided with the ground reaction force measuring unit 300*b*.

For example, the ground reaction force measuring unit 300*b* may be disposed under the sole of the object to be measured.

Further, the ground reaction force measuring unit 300*b* may include a pressure sensor, a piezoelectric plate, a strain gauge, or the like.

However, a form and a disposition of the ground reaction force measuring unit 300*b* are not limited thereto, and therefore the ground reaction force measuring unit 300*b* may have various forms and may be disposed at various positions.

In detail, the strength of force applied to the ground reaction force measuring unit 300*b* by the lower extremities of the object to be measured may be changed when the object to be measured sits on or separated from the sitting part 100*b*.

For example, the strength of force applied to the ground reaction force measuring unit 300*b* by the lower extremities of the object to be measured may be largely measured when the object to be measured is separated from the sitting part 100*b*.

Further, it is possible to predict the paralysis state of the lower extremities based on the left and right ratio of the size of the ground reaction force measured by the ground reaction force measuring unit 300*b*.

If the size of the ground reaction force measured by the ground reaction force measuring unit 300*b* is relatively small, the paralysis state of the lower extremities may be in a serious state and if the size of the ground reaction force measured by the ground reaction force measuring unit 300*b* is relatively larger, the paralysis state of the lower extremities may be in a less serious state.

Further, the ground reaction force measuring unit 300*b* may be configured to include a first measurement element 310*b* provided at a lower portion of one lower extremity and a second measurement element 320*b* provided at a lower portion of the other lower extremity.

In detail, the first measurement element 310*b* may be provided under the right lower extremity of the object to be measured, for example, under the right sole and the second measurement element 320*b* may be provided under the left lower extremity of the object to be measured, for example, under the left sole.

The first measurement element 310*b* may measure the ground reaction generated by the right lower extremity and the second measurement element 320*b* may measure the ground reaction force generated by the left lower extremity.

For example, when the object to be measured sitting on the sitting part 100*b* is instructed to stand up as slowly as possible while applying the force to the right lower extremity as much as possible, if the muscle strength of the right lower extremity of the object to be measured is strong, the object to be measured may stand up while applying most of the body weight load to the right lower extremity, such that the first measurement element 310*b* may measure the large ground reaction force.

However, if the muscle strength of the right lower extremity of the object to be measured is weak, the object to be measured may stand up while applying only some of the body weight load to the right lower extremity, such that the first measurement element 310*b* may measure the relatively smaller ground reaction force.

Further, when the object to be measured sitting on the sitting part 100*b* is instructed to stand up as slowly as possible, the ratio of ground reaction forces measured by the first measurement element 310*b* and the second measurement element 320*b*, respectively, may be changed according to the muscle strength of the lower extremity to be measured.

For example, when the object to be measured rises as slow as possible while applying the body weight to the right lower extremity as much as possible, if the ratio of ground reaction forces measured by the first measurement element 310*b* and the second measurement element 320*b*, respectively is 5:5, it is possible to evaluate that the right lower extremity may support 50% of the body weight when the object to be measured stands up.

On the other hand, when the ratio of ground reaction forces measured by the first measurement element 310*b* and the second measurement element 320*b*, respectively is 7:3, it is possible to evaluate that the right lower extremity may support 70% of the body weight when the object to be measured rises.

The ratio is relative, and therefore a moving speed, a height of a sitting part (a chair), and a height and a weight of a patient may be substituted using a conversion equation or a table to calculate an absolute value.

As such, it is possible to measure the lower extremity muscle strength as well as the paralysis state and the exercise state of the lower extremities based on the size or the ratio of left and right ground reaction forces measured by the ground reaction force measuring unit 300*b*.

The control unit 400*b* may calculate the lower extremity muscle strength based on the ground reaction force measured by the ground reaction force measuring unit 300*b*.

In particular, referring to FIG. 8, the control unit 400*b* may analyze or determine the change in the size of the ground reaction force over time.

First, the control unit 400*b* may measure the lower extremity muscle strength based on the size and the ratio of left and right ground reaction forces when the sum of the left and right ground reaction forces is highest. As illustrated in FIG. 8, the ratio of the size of the left and right ground reaction forces may also be changed over time while the size of the left and right ground reaction forces is changed over time.

The size of the muscle contraction required to make the object to be measured stand up is largest at the timing when the object to be measured is separated from the sitting part 100*b*, and therefore the timing when the left and right ground reaction forces are largest may be used as the timing when the object to be measured is separated from the sitting part 100*b*.

In FIG. 8, the sum of the ground reaction forces is largest at 1.5 seconds and the sum of the ground reaction forces becomes approximately 110 (% BM). In this case, the ground reaction force of the paralyzed lower extremity becomes approximately 40 (% BM) and the ground reaction force of the non-paralyzed lower extremity becomes approximately 70 (% BM).

For example, the paralyzed lower extremity may be the right lower extremity and the non-paralyzed lower extremity may be the left lower extremity.

In other words, when the body weight of the object to be measured is 100 kgf, the total ground reaction force of the object to be measured may be 110 kgf and the ground reaction force of the right lower extremity among them may be 40 kgf and the ground reaction force of the left lower extremity may be 70 kgf.

As such, it may know that the subject may rise by how much a weight body is applied to the muscle strength of the paralyzed lower extremity and the non-paralyzed lower extremity based on the ratio of left and right ground reaction forces measured as described above.

Further, when the sum of the left and right ground reaction forces is highest, the ratio of ground reaction force of the paralyzed lower extremity and the ground reaction force of the non-paralyzed lower extremity may be 4:7.

In this case, if the weight body load of the lower extremities is calculated based on the ground reaction force when the sum of the left and right ground reaction forces is highest, it may be considered that 36% (=4/11*100) of the total weight body is a load for the paralyzed lower extremity and 63 (7/11*100) % of the total weight body is a load for the non-paralyzed lower extremity.

Therefore, when the sum of the left and right ground reaction forces is highest, the weight body load of the respective lower extremities may be understood based on the size and the ratio of left and right ground reaction forces and the muscle strength of the left and right lower extremities may be measured based on the weight body load.

Second, the control unit 400*b* may measure the lower extremity muscle strength based on the area drawn by the ground reaction force.

In detail, when the object to be measured stands up in the state in which it sits on the sitting part 100*b*, a graph from the timing (for example, 1.2 seconds) when the total ground reaction force is larger than a stable state to the timing (for example, 1.5 seconds) when the total ground reaction force is highest is accumulated and thus the ground reaction force may be compared by the area thereof.

For example, when the object to be measured sitting on the sitting part 100*b* is instructed to stand up while applying the force to the right lower extremity as much as possible, if 'a value obtained by accumulating a section of the graph drawn by the right ground reaction force' is divided by 'a value obtained by accumulating a section of the graph drawn by the total ground reaction force', it is possible to know that the object to be measured stands up by how large a force is applied to the right lower extremity when the object to be measured stands up.

To the contrary, when the object to be measured sitting on the sitting part 100*b* is instructed to stand up while applying the force to the left lower extremity as much as possible, if 'a value obtained by accumulating a section of the graph drawn by the left ground reaction force' is divided by 'a value obtained by accumulating a section of the graph drawn by the total ground reaction force', it is possible to know that the object to be measured stands up by how large a force is applied to the left lower extremity when the object to be measured stands up.

By doing so, it is possible to predict the muscle strength or the paralysis state of the right or left lower extremity.

As such, the control unit 400*b* may analyze or determine the muscle strength or the paralysis state of the lower extremities.

The control unit 400*b* may be connected to the display unit 500*b* and contents analyzed or determined by the control unit 400*b* may be fed back in real time through the display unit 500*b*.

For example, a medical team may visually confirm the rehabilitation state of a patient and a user may easily recognize the rehabilitation state based on figures or characters.

Further, a system for measuring lower extremity muscle strength according to another embodiment of the present invention may access the game server to interact with the game or Internet based virtual world, and therefore is having fun while performing rehabilitation treatment, thereby effectively performing the rehabilitation treatment.

In this case, the game may be performed based on the size and the ratio of left and right ground reaction forces measured by the ground reaction force measuring unit 300*b*.

For example, the rehabilitation exercise of the user may be induced to more strengthen the lower extremity with weak muscle strength based on the lower extremity muscle strength measured by means of the size and the ratio of left and right ground reaction forces.

Further, the motion of the characters may be controlled according to the rehabilitation exercise of the user and the user may perform the rehabilitation exercise, having an interest according to a kind of games.

In addition, when the user performs game along with the other person, competitive spirit is aroused and thus the user may positively participate in the rehabilitation exercise.

Here, the control unit 400*b* and the display unit 500*b* of the apparatus for measuring lower extremity muscle strength according to another embodiment of the present invention are provided in portable terminals such as a PC and a smart phone to easily determine and analyze the muscle strength or the paralysis state of the lower extremity and feedback the content thereof.

As such, the apparatus for measuring lower extremity muscle strength according to another embodiment of the present invention may use the camera, the motion capturer, the motion sensor, the switch, or the like to effectively figure out the timing when the object to be measured is separated from the sitting part, use the size and the left and right ratio of the ground reacting force of the lower extremity at the timing when the object to be measured is separated from the sitting part to measure the paralysis degree of the lower extremity muscle strength and the lower extremity muscle strength, use the area drawn by the ground reacting force to measure the paralysis degree of the lower extremity muscle strength and the lower extremity muscle strength, and use the size and the ratio of left and right ground reaction forces to train the lower extremities.

Hereinabove, although the present invention has been described by specific matters such as detailed components, exemplary embodiments, and the accompanying drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims to be described below and all of modifications equal or equivalent to the claims are intended to fall within the scope and spirit of the present invention.

[Detailed Description of Main Elements]

First Embodiment

10a: System for measuring lower extremity muscle strength
100a: Sitting part
200a, 210a: Sensing unit
212a: First sensing element
214a: Second sensing element
300a: Ground reacting force measuring unit
310a: First ground reacting force measuring unit
320a: Second ground reacting force measuring unit
400a: Control unit Second Embodiment 10b: System for measuring lower extremity muscle strength
100b: Sitting part
200b: Posture measuring unit
210b: Camera
220b: Motion capturer
222b: Patch
224b: Camera
230b: Motion sensor
232b: Band
240b: Switch
300b: Ground reacting force measuring unit
310b: First measurement element
320b: Second measurement element
400b: Control unit
500b: Display unit

The invention claimed is:

1. A system for measuring lower extremity muscle strength, comprising:
a sitting part on which an object to be measured sits, wherein the sitting part is a chair, table, or flat surface;
a sensing unit mounted on the sitting part or at a portion of the object to be measured contacting the sitting part, wherein the sensing unit senses whether the object to be measured is separated from the sitting part;
a ground reaction force measuring unit measuring over time a first and a second ground reaction forces generated by lower extremities of the object to be measured, the ground reaction force measuring unit comprising:
a first ground reaction force measuring unit configured to measure the first ground reaction force of one of the lower extremities; and
a second ground reaction force measuring unit configured to measure the second ground reaction force of the other of the lower extremities;
and a control unit,
wherein the control unit is configured to determine a first timing when a sum of the first and the second ground reaction forces is largest and confirms the first timing as a timing of separation, which is defined as a timing at which the object is separated from the sitting part, and wherein the control unit is configured to determine a paralysis state for each of the lower extremities based on sizes and a ratio of the first and the second ground reaction forces at the timing of separation.

2. The system of claim 1, wherein the sensing unit is configured to sense a moment that a hip or a thigh of the object to be measured is separated from the sitting part.

3. The system of claim 1, wherein the sensing unit is provided as a switch mounted at a hip or a thigh of the object to be measured, and wherein the switch is switched to an on or off state when the hip or the thigh of the object to be measured is separated from the sitting part.

4. The system of claim 1, wherein the sensing unit comprises a first sensing element mounted at a hip or a thigh of the object to be measured and a second sensing element mounted on the sitting part, and wherein the sensing unit is configured to provide information on timing when the hip or the thigh of the object to be measured is separated from the second sensing element.

5. The system of claim 1, wherein the sensing unit includes:
a first sensing element mounted at a hip or a thigh of the object to be measured; and
a second sensing element mounted at a position contacting the first sensing element at the sitting part.

6. The system of claim 1, wherein the ground reaction force measuring unit includes a piezoelectric plate or a strain gauge.

7. The system of claim 1,
wherein the control unit is configured to calculate lower extremity muscle strengths based on the ground reaction forces measured by the ground reaction force measuring unit.

8. A system for measuring lower extremity muscle strength, comprising:
a sitting part on which an object to be measured sits, wherein the sitting part is a chair, table, or flat surface;
a posture measuring unit configured to measure a posture of the object to be measured;
a ground reaction force measuring unit disposed at a lower portion of the object to be measured and configured to measure a ground reaction force generated by one of lower extremities of the object to be measured; and a control unit, wherein a lower extremity muscle strength of the object to be measured is determined based on the ground reaction force at a moment where the object to be measured is separated from the sitting part or a ratio of the ground reaction force; and wherein the control unit is configured to confirm a timing and the ground reaction force when the object to be measured is separated from the sitting part and determines a paralysis state of the lower extremity.

9. The system of claim 8, wherein the posture measuring unit is provided as a camera and is configured to sense the moment that the object to be measured is separated from the sitting part by the camera.

10. The system of claim 8, wherein the posture measuring unit is provided as a motion capturer and is configured to sense the moment that the object to be measured is separated from the sitting part by the motion capturer.

11. The system of claim 8, wherein the posture measuring unit is provided as a motion sensor including a gyro sensor or an acceleration sensor and is configured to sense the moment that the object to be measured is separated from the sitting part by the motion sensor.

12. The system of claim 8, wherein the sensing unit is provided as a switch mounted at a hip or a thigh of the object to be measured, and wherein the switch is switched to an on or off state when the hip or the thigh of the object to be measured is separated from the sitting part.

13. The system of claim 8, wherein the ground reaction force measuring unit includes:

a first measurement element provided at a lower portion of one of the lower extremities and configured to measure a first ground reaction force of the one of the lower extremities; and a second measurement element provided at a lower portion of the other of the lower extremities and configured to measure a second ground reaction force of the other of the lower extremities.

14. The system of claim 13, wherein the system evaluates the lower extremity muscle strength based on a ratio of the first ground reaction force measured by the first measurement element and the second ground reaction force measured by the second measurement element.

15. The system of claim 8, wherein the control unit is configured to calculate the lower extremity muscle strength based on the ground reaction force measured by the ground reaction force measuring unit.

16. The system of claim 8, wherein the control unit is connected to a display unit and contents analyzed or determined by the control unit are fed back in real time through the display unit.

17. The system of claim 8, wherein the ground reaction force measuring unit includes a pressure sensor, a piezoelectric plate or a strain gauge.

* * * * *